US007695988B2

(12) United States Patent
Stavis et al.

(10) Patent No.: US 7,695,988 B2
(45) Date of Patent: Apr. 13, 2010

(54) QUANTUM DOT CONJUGATES IN A SUB-MICROMETER FLUIDIC CHANNEL

(75) Inventors: Samuel M. Stavis, Ithaca, NY (US);
Joshua B. Edel, Brookline, MA (US);
Kevan T. Samiee, Ithaca, NY (US);
Harold G. Craighead, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 43 days.

(21) Appl. No.: 12/143,334

(22) Filed: Jun. 20, 2008

(65) Prior Publication Data

US 2009/0116007 A1    May 7, 2009

Related U.S. Application Data

(63) Continuation of application No. 11/280,941, filed on Nov. 16, 2005, now Pat. No. 7,405,434.

(60) Provisional application No. 60/628,161, filed on Nov. 16, 2004.

(51) Int. Cl.
*G01R 31/26* (2006.01)
*H01L 21/66* (2006.01)

(52) U.S. Cl. .................. 438/14; 438/962; 257/E29.071; 977/700; 977/774

(58) Field of Classification Search ...................... 438/6, 438/16, 146; 257/14, 107
See application file for complete search history.

(56) References Cited

U.S. PATENT DOCUMENTS 6,346,431 B1    2/2002    Yoo et al.

| 7,105,354 | B1 | 9/2006 | Shimoide et al. |
| 2003/0148544 | A1 | 8/2003 | Nie et al. |
| 2007/0020779 | A1 | 1/2007 | Stavis et al. |

OTHER PUBLICATIONS

"U.S. Appl. No. 11/280,941 Notice of Allowance mailed Mar. 21, 2008", NOAR,11 Pgs.
"Mathtools.net > Java > Optimization . MATLAB", http://web.archive.org/web/20040110133154/http://mathtools.net/Java/Optimization/MATLAB/, (archived Jan. 10, 2004),2 pgs.
Auroux, P.-A. , et al., "Micro Total Analysis Systems. 2. Analytical Standard Operations and Applications", *Analytical Chemistry*, 24(12), (Jun. 15, 2002),2637-2652.

(Continued)

*Primary Examiner*—Alexander G Ghyka
*Assistant Examiner*—Abdulfattah Mustapha
(74) *Attorney, Agent, or Firm*—Schwegman, Lundberg & Woessner, P.A.

(57) ABSTRACT

A nanofluidic channel fabricated in fused silica with an approximately 500 nm square cross section was used to isolate, detect and identify individual quantum dot conjugates. The channel enables the rapid detection of every fluorescent entity in solution. A laser of selected wavelength was used to excite multiple species of quantum dots and organic molecules, and the emission spectra were resolved without significant signal rejection. Quantum dots were then conjugated with organic molecules and detected to demonstrate efficient multicolor detection. PCH was used to analyze coincident detection and to characterize the degree of binding. The use of a small fluidic channel to detect quantum dots as fluorescent labels was shown to be an efficient technique for multiplexed single molecule studies. Detection of single molecule binding events has a variety of applications including high throughput immunoassays.

23 Claims, 12 Drawing Sheets

OTHER PUBLICATIONS

Bacia, K., et al., "A Dynamic View of Cellular Processes by in vivo Fluorescence Auto- and Cross-Correlation Spectroscopy", *Methods*, 29, (2003),74-85.

Basche, T., et al., "Dynamical Processes of Single Molecules as Deduced From the Fluorescence Autocorrelation Function", *Experimental Technique of Physics* (Germany), 41(2), Conference Title: International Workshop 'Single Molecule Detection: Basics and Applications in Life Sciences',(1995),197-204.

Chon, J. W., et al., "Scanning Total Internal Reflection Fluorescence Microscopy Under One-Photon and Two-Photon Excitation: Image Formation", *Applied Optics*, 43(5), (Feb. 10, 2004),1063-1071.

De Mello, A. J., et al., "Seeing Single Molecules", *Lab on a Chip*, 3, (2003),29N-34N.

Dekel, E., et al., "Optical Spectroscopy of a Single Self-Assembled Quantum Dot", *Physica E-Low-Dimensional Systems & Nanostructures*, 2, (1998),694-700.

Dittrich, P. S., et al., "Spatial Two-Photon Fluorescence Cross-Correlation Spectroscopy for Controlling Molecular Transport in Microfluidic Structures", *Analytical Chemistry*, 74(17), (2002),4472-4479.

Edel, J. B., et al., "Continuous Real-Time Monitoring of Quantum Dot Synthesis Within Microfluidic Reactors", *Proceedings of the 7th International Conference on Micro Total Analysis Systems*, (2003),673-676.

Edel, J. B., et al., "Velocity Measurement of Particulate Flow in Microfluidic Channels Using Single Point Confocal Fluorescence Detection", *Analyst*, 126, (2001),1953-1957.

Foquet, M., et al., "DNA Fragment Sizing by Single Molecule Detection in Submicrometer-Sized Closed Fluidic Channels", *Analytical Chemistry*, 74(6), (Mar. 15, 2002),1415-1422.

Foquet, M., et al., "Focal Volume Confinement by Submicrometer-Sized Fluidic Channels", *Analytical Chemistry*, 76(6), (2004),1618-1626.

Harms, G. S., et al., "Autofluorescent Proteins in Single-Molecule Research: Applications to Live Cell Imaging Microscopy", *Biophysical Journal*, 80, (May 2001),2396-2408.

Levene, M. J., et al., "In Vivo Multiphonton Microscopy of Deep Brain Tissue", *Journal of Neurophysiology*, 91(4), (2004),1908-1912.

Magde, D., et al., "Fluorescence Correlation Spectroscopy. III. Uniform Translation and Laminar Flow", *Biopolymers*, 17, (1978),361-376.

Mattheakis, L. C., et al., "Optical Coding of Mammalian Cells Using Semiconductor Quantum Dots", *Analytical Biochemistry*, 327, (2004),200-208.

Michalet, X., et al., "Single-Molecule Spectroscopy and Microscopy", *Comptes Rendus Physique*, 3, (2002),619-644.

Moerner, W. E., "Single-Molecule Optical Spectroscopy of Autofluorescent Proteins", *Journal of Chemical Physics*, 117(24), (Dec. 22, 2002),10925-10937.

Peck, K., et al., "Single-Molecule Fluorescence Detection: Autocorrelation Criterion and Experimental Realization With Phycoerythrin", *Proc. Natl. Acad. Sci. USA*, 86, (Jun. 1989),4087-4091.

Protasenko, V. V., et al., "Factors That Influence Confocal Apertureless Near-Field Scanning Optical Microscopy", *Optics Communications*, 233, (2004),45-56.

Ramsey, J. M., et al., "Looking for Single Molecules in Small Droplets", *Abstracts of Papers of the American Chemical Society*, (presented at the 198th ACS National Meeting) (Abstract ANYL-74),(1989),1 pg.

Reyes, D. R., et al., "Micro Total Analysis Systems. 1. Introduction, Theory, and Technology", *Analytical Chemistry*, 74(12), (Jun. 15, 2002),2623-2636.

Schwille, P., "Dual-Color Fluorescence Cross-Correlation Spectroscopy for Multicomponent Diffusional Analysis in Solution", *Biophysical Journal*, 72(4), (Apr. 1997),1878-1886.

Wagner, B., et al., "Single Molecule Detection in Microstructures", *Nucleosides & Nucleotides*, 16(5&6), (1997),635-642.

Zhong, Z.-H., et al., "Insulin Binding Monitored by Fluorescence Correlation Spectroscopy", *Diabetologia*, 44, (2001),1184-1188.

ns which Fluor 488 molecules

QUANTUM DOT CONJUGATES IN A SUB-MICROMETER FLUIDIC CHANNEL

RELATED APPLICATION

This application is a continuation application of U.S. patent application Ser. No. 11/280,941, filed Nov. 16, 2005, now U.S. Pat. No. 7,405,434 which claims the benefit of U.S. Provisional Application Ser. No. 60/628,161 (entitled QUANTUM DOT CONJUGATES IN A SUBMICROMETER FLUIDIC CHANNEL, filed Nov. 16, 2004) which applications are incorporated herein by reference.

GOVERNMENT FUNDING

The invention described herein was made with U.S. Government support under Grant Number DE-FG02-99ER62809 awarded by the Department of Energy. The United States Government has certain rights in the invention.

BACKGROUND

The development of microfluidics and lab-on-a-chip technology has been driven in part by the objective of rapid analysis and reduction of reagent and analyte consumption. There is also a strong drive to obtain assays with high detection sensitivity while providing rapid analysis and reduction of reagent and analyte consumption.

SUMMARY

A nanofluidic channel sized to promote single molecule flow may be used to isolate, detect and identify individual quantum dot conjugates. The channel enables the rapid detection of every fluorescent entity in solution. A laser of selected wavelength may be used to excite multiple species of quantum dots and molecules, and emission spectra may be resolved without significant signal rejection.

DETAILED DESCRIPTION

Figure 1A:
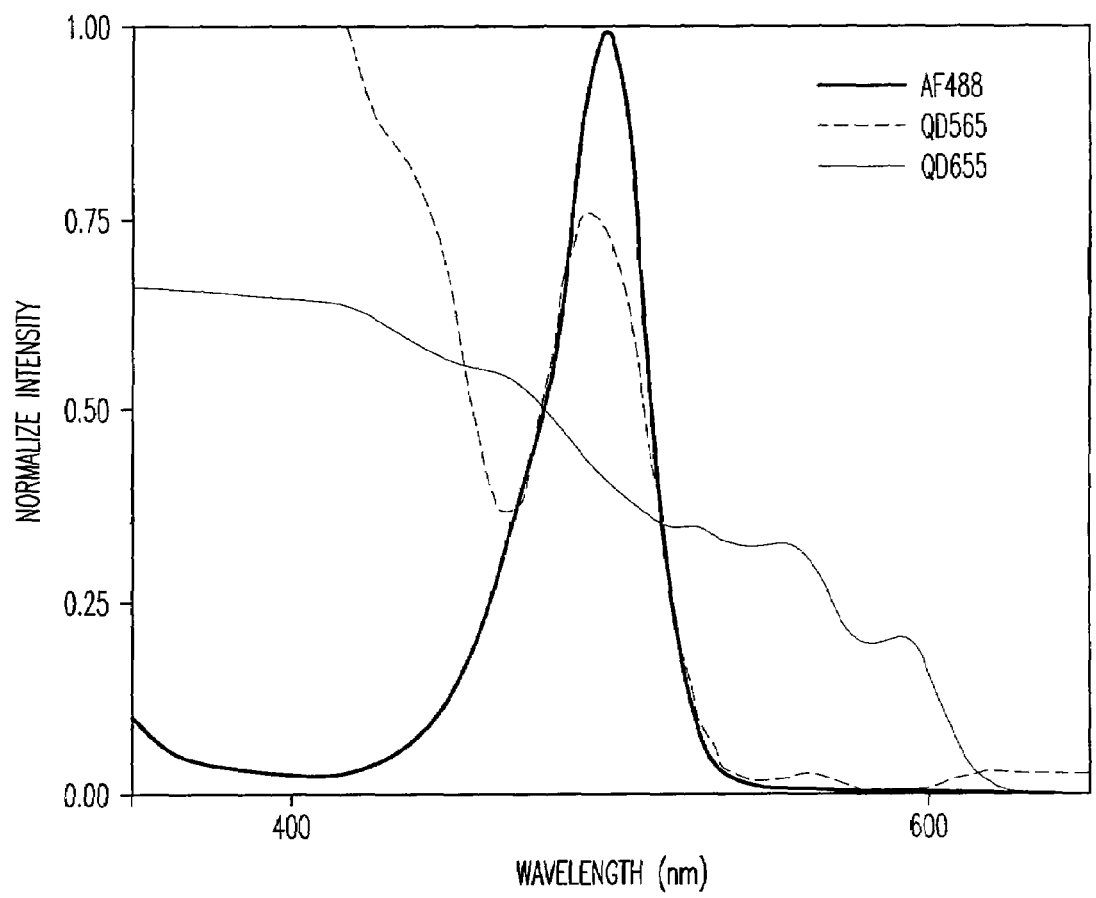
FIGS. 1A and 1B illustrate absorption and emission spectra of Alexa Fluor 488, Qdot 565 and Qdot 655 according to an example embodiment.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description is, therefore, not to be taken in a limited sense, and the scope of the present invention is defined by the appended claims.

A device for detecting quantum dots conjugated with different types of molecules is described. Two similar methods for fabricating the device are described, along with two methods for detecting different types of molecules conjugated with quantum dots. The device structure of a nanofluidic channel combined with optics for excitation and detection is similar for both embodiments.

Selection of fluorescent labels is an essential parameter in any fluorescence microscopy assay and especially in single molecule studies. Label selection is guided primarily by the necessity of having a signal to noise ratio large enough that single molecules can be detected and analyzed. Quantum dots are exceptionally bright and photostable, making them valuable in this regard for single molecule studies. In a multicolor experiment there are considerations beyond the basic ability to detect single molecules, such as the spectral properties of the fluorescent labels. In order to isolate fluorescent emission from a single species of fluorophore, the Stokes shift must be large enough to resolve the emission and excitation peaks. In a multicolor experiment, this situation can be complicated by multiple fluorescent species with overlapping emission and excitation spectra. Quantum dots have several spectral characteristics that avoid these problems and make them desirable for use in multicolor single molecule studies. Compared to standard ionic or organic fluorophores, quantum dots display an enormous Stokes shift. Additionally, quantum dots with different emission wavelengths can be excited by the same excitation source, typically in the blue part of the visible spectrum. The union of these traits results in the ability to simultaneously excite several species of quantum dots with a single light source, while their emission spectra are easily and entirely resolved.

A microfluidic and optical system enables analysis of single molecules. An array 200 of fluidic channels 210 with at least submicrometer fluid (nanofluidic) channel portions 220 having submicrometer dimensions may be used to isolate, detect and identify individual quantum dots conjugated with organic fluorophores in solution. In one embodiment illustrated in FIG. 2A and FIG. 2B, channels may be fabricated in fused silica with a 500 nm square cross section. The resulting focal volume of approximately 210 zL reduces fluorescent background and increases the signal to noise ratio of single molecule detection. The channel also enables the rapid detection of greater than 99% of quantum dots and organic fluorophores traversing the focal volume.

The submicrometer fluid channel, also referred to as a nanofluidic channel, is a nanofabricated structure, which physically constrains the sample in two dimensions, one lateral and one axial, further reducing the number of unwanted fluorophores detected. Another property of the nanofluidic channels is the ability to flow single molecules through the detection volume with a high degree of control. This enables a balance of several factors important to single molecule detection and analysis, including detection efficiency and rates of throughput and data acquisition. While the nanofluidic channel has been described as a channel having a cross section of approximately 500 nm square, other sizes of channels having similar characteristics may be used, such as channels having smaller, or larger cross sections.

Conjugates may be driven through the channel electrokinetically at 100 V/cm, excited with a 476 nm wavelength laser in one embodiment, and detected with a confocal microscope. Fluorescence emission may be collected simultaneously from green (500-590 nm) and red (610-680 nm) regions of the spectrum. Signal rejection is minimized by the narrow and symmetric emission spectra of the quantum dots. Other means may also be used to drive the conjugates through the nanochannels, such as pressure based devices, centrifugal force, hydrostatic and gravity based drivers.

To verify the absence of spectral cross talk, two quantum dot conjugates may be detected both separately and simultaneously in solution, including Qdot 565 Streptavidin Conjugates and Qdot 655 Streptavidin Conjugates. To demonstrate efficient multicolor detection and characterization of binding, Qdot 655 Streptavidin Conjugates may be bound to Alexa Fluor 488 molecules and individually detected. Photon counting histogram analysis may be used to quantify coincident detection and degree of binding. Fluorescence correlation spectroscopy may be used to account for possible mobility differences between the bound and unbound species. The union of fluidic channels with submicrometer dimensions and quantum dots as fluorescent labels may be used for efficient, rapid and complete multiplexed single molecule detection and analysis.

Single molecules may be detected at low concentrations by optically detecting the binding of a single labeled molecule to a functionalized quantum dot. Selection of fluorescent labels is an essential parameter in optical single molecule studies, and quantum dots have attracted interest as an emerging technology in this regard. Quantum dots have diverse applications, and have recently been studied in a variety of fluorescence microscopy and biological assays. Single quantum dots have been detected using a variety of microscope configurations, including with a diffraction-limited spot, with near-field scanning optical microscopy and on a substrate using total internal reflection microscopy. Quantum dots have also been used as fluorescent labels in live cells and for in vivo multiphoton microscopy. Because of their unique and beneficial optical properties, quantum dots have potential as fluorescent labels in single molecule studies.

Label selection is guided primarily by the necessity of having a signal to noise ratio large enough that single molecules can be detected and analyzed. Because of their high extinction coefficients and quantum yields, quantum dots are exceptionally bright, making them valuable for single molecule studies. Quantum dots are also highly photostable. In a multicolor experiment there are considerations beyond the basic ability to detect single molecules, such as the spectral properties of the fluorescent labels. In order to isolate fluorescence emission from a single species of fluorophore, the Stokes shift must be large enough to resolve the emission and excitation peaks. In a multicolor experiment, this situation can be complicated by multiple fluorescent species with overlapping emission and excitation spectra. Typically, when standard organic fluorophores are used, overlap in the emission spectra is managed by restricting the spectral range of collected fluorescence. This results in rejected signal and reduced detection efficiency.

Figure 1B:
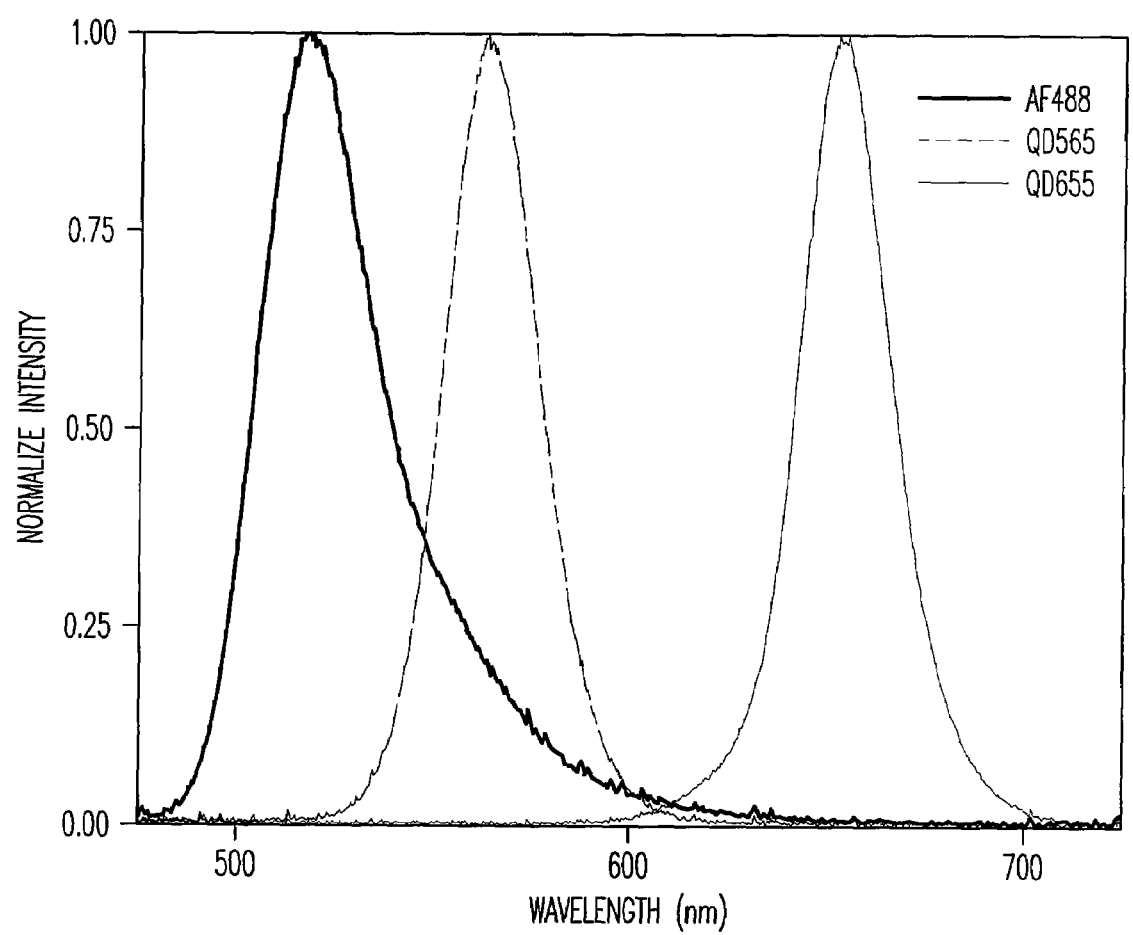

Quantum dots have several spectral characteristics that avoid these problems and make them desirable for use in multicolor single molecule studies. Compared to standard organic fluorophores, quantum dots have narrow and symmetrical emission spectra. Quantum dots also display a large effective Stokes shift, and different quantum dots can be excited by the same excitation source, typically in the blue part of the spectrum. The union of these traits results in the ability to simultaneously excite several species of quantum dots, or combinations of quantum dots and organic fluorophores, with a single light source, while the emission spectra are easily and entirely resolved. The absorption spectra of quantum dots, Qdot 565, Qdot 655 and Alexa Fluor 488 are shown in FIG. 1A, and the emission spectra are shown in FIG. 1B. Alexa Fluor 488 shows an absorbance peak with the characteristic shape of an organic fluorophore, whereas the quantum dots are excited over a broader range of wavelengths. Any of the three species can be excited simultaneously with a single source, in this embodiment, at 476 nm. FIG. 1B shows emission spectra of Qdot 565, Qdot 655 and Alexa Fluor 488. Because of their narrow emission peaks, there is virtually no spectral overlap between the two quantum dots. Alexa Fluor 488 displays a wider emission peak with a long tail at higher wavelengths, characteristic of ionic dyes. This increased detection efficiency is particularly relevant in single molecule detections where signal to noise ratio is often a limiting factor.

Focal volume reduction may be used to achieve a signal to noise ratio high enough to isolate and detect single quantum dot conjugates. By reducing the focal volume, the number of unwanted fluorescent molecules and corresponding background noise may be diminished. Two means may be used to achieve focal volume reduction, either alone, or combined. A first level of confinement may be obtained via a confocal microscope with high numerical aperture optics, which confines collection of fluorescence to the depth of focus of the objective. The second utilizes a small fluidic channel, which physically constrains the sample in two dimensions, the width and the depth, further reducing the number of unwanted fluorophores detected.

In one embodiment, the submicrometer fluidic channels 220 transport single molecules through the detection volume with a high degree of control. This may enable a balance of several factors for single molecule detection and analysis, including detection efficiency, rates of throughput and data acquisition. Fluidic channels are also ideally suited for parallel integration with high throughput lab-on-a-chip applications.

In one example, to verify the absence of spectral cross talk in this microfluidic-optical system, two quantum dot conjugates were analyzed, including Qdot 565 Streptavidin Conjugates and Qdot 655 Streptavidin Conjugates. The two species were detected separately as a control and together to demonstrate negligible cross-correlation. After spectral cross talk was confirmed to be absent, Qdot 565 Streptavidin Conjugate was bound to a short DNA oligomer labeled with Alexa Fluor 488 and biotinylated at the 3' end. Unbound quantum dots and DNA molecules were detected as temporally separate photon bursts in the two color channels. When bound together, the two species were detected simultaneously as they crossed the focal volume. Photon Counting Histogram (PCH) analysis was used to quantify coincident detection and to characterize the binding processes of the conjugates. Fluorescence correlation spectroscopy was used to account for possible mobility differences. In all cases, the samples were diluted to a concentration of several hundred pM to minimize the possibility of multiple quantum dot conjugates passing through the detection volume simultaneously.

A fluidic channel with submicrometer dimensions used in conjunction with a confocal microscope to detect individual quantum dots and fluorophores was shown to be an efficient technique for single molecule studies. Because of the spectral properties of the quantum dots, a single excitation source was used for all quantum dots and organic fluorophores, and signal rejection was minimized. The channel enabled the rapid detection of greater than 99% of quantum dots and organic fluorophores crossing the focal volume.

Figure 2A:
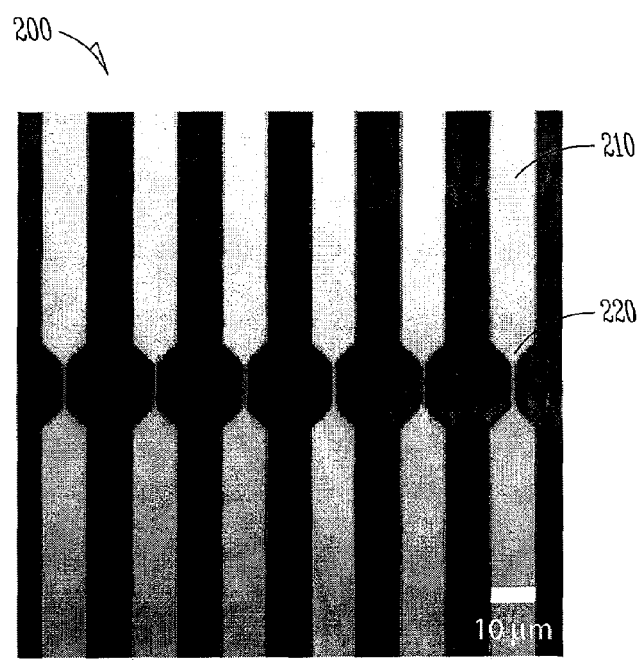
FIGS. 2A and 2B are a schematic of a fluidic channel and the associated detection volume as defined by a focused laser beam according to an example embodiment.
Figure 2B:
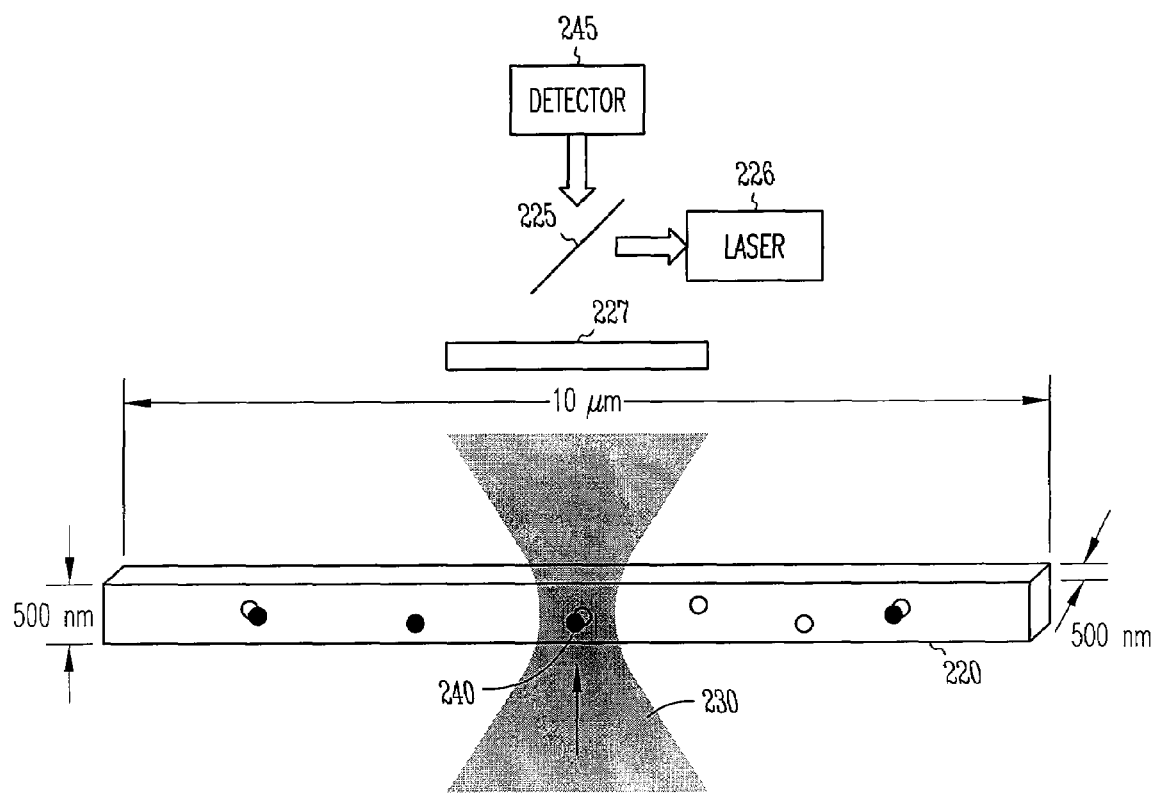

The material properties of the channels as shown in FIGS. 2A and 2B were selected to provide correct device operation and the ability to detect single molecules. Optical properties were of primary concern in this regard, and the main goal of material selection was to minimize autofluorescence and maximize signal to noise ratio. In one embodiment, a mirror-polished fused silica substrate and cover wafers (Mark Optics Incorporated, Santa Ana, Calif.), 500 µm and 170 µm thick respectively, were chosen for this reason. Additional benefits of using fused silica include its excellent thermal, mechanical and chemical properties, making the nanofluidic channels durable as well as functional under a wide variety of solution chemistries and operating conditions.

Devices may be fabricated using standard photolithographic processes in conjunction with a fusion bonding technique. This combination was chosen for its simplicity, high throughput and low cost. A thin film of photoresist may be spun onto the fused silica substrate for both pattern transfer and for use as an etch mask. An optical mask produced with a pattern generator may be used to expose the positive device pattern in the photoresist. After development, a $CF_4$ RIE may be used to etch the channels to a depth of approximately 500 nm. This provides a square channel cross section, as well as smooth channel surfaces. Etching to a depth slightly less than the channel width may be used to provide some degree of automatic filtration to prevent clogs, often an issue in fluidic channels. Inlet and outlet holes may be formed through the substrate using an alumina powder blaster. The substrate and cover wafers may be cleaned, including a final RCA base bath clean. After the wafers are cleaned and dried, they may be placed in physical contact and mechanical pressure applied, creating a weak initial bond. A high temperature anneal may be used to make the initial bond permanent.

FIG. 2A is an optical micrograph of an example parallel array of fluidic channels formed using the above process. Many other methods may be used to form such channels, and the steps described above may be modified as desired. Nanoport fluidic connectors, (such as those available from Upchurch Scientific, Oak Harbor, Wash.) may be attached to the wafers at an inlet reservoir coupled to the channels. Polyethylene reservoirs may be attached to a waste outlet of the devices. Devices may be filled with hydrostatic pressure, and gold electrodes placed in the channel reservoirs to enable electrokinetic drive of a solution through the channels. A 100 V bias may be applied across the two reservoirs, which in one embodiment have an approximately 1.0 cm length between them.

In one example, to demonstrate efficient multicolor detection with quantum dots and organic fluorophores, Qdot 655 Streptavidin Conjugate (Quantum Dot Corporation, Hayward, Calif.) was bound to Alexa Fluor 488 via a DNA oligomer consisting of 28 thiamine residues biotinylated at the 3' end. The Alexa Fluor 488 was attached to the 5' end of the oligomer (Operon Biotechnologies, Alameda, Calif.). Equal volumes of 200 nM DNA oligomer solution and 20 nM quantum dot solution were mixed. The mixture was then incubated at 37° C. for 30 minutes and stored at 2° C. for approximately 60 hours before dilution to several hundred pM in TBE 1× buffer with 1% by volume NP-40 and analysis.

An inverted confocal microscope was used in conjunction with a fluidic channel to detect single quantum dots and organic fluorophores. The entire setup rested on a floating optical table (TMC, Peabody, Mass.) to isolate the microscope, laser and optical equipment from vibrations. An Olympus IX71 inverted microscope (Olympus America, Melville, N.Y.) with an integrated Prior Pro-Scan stage (Prior Scientific Incorporated, Rockland, Mass.) formed the core of the experimental setup. An Argon-Krypton mixed gas tunable laser (Melles Griot Laser Group, Carlsbad, Calif.) was used for excitation at 476 nm. Between the laser aperture and microscope, a number of optical elements were used to guide and tune the laser beam, including mirrors, kinematic mounts optics and irises (Newport Corporation, Irvine, Calif.). A neutral density filter wheel was used for laser attenuation (Thorlabs Incorporated, Newton, N.J.).

A 497 nm dichroic mirror 225 reflected the 476 nm laser 226 light towards the channel, where an Olympus UPlanAPO 60X coverslip-corrected water immersion objective 227 was used in epifluorescence mode to both focus the laser beam 230 on the channel for excitation and to collect emitted fluorescence. The back aperture of the objective was underfilled in order to deliver maximum laser power along with an approximately uniform laser profile across the channel.

A schematic of the fluidic channel 220 and detection volume as defined by the focused laser 230 can be seen in FIG. 2B. The focused laser spot 230 was determined to have a 1/e size of at least 1.4 µm, from free solution diffusion measurements (not shown) of dUTP labeled with Alexa Fluor 488 (Molecular Probes Incorporated, Eugene, Oreg.) shown traversing the channel at 240. Collected fluorescence was directed back through the 497 nm dichroic mirror 225 to a 520 nm long pass barrier filter and detector 245. A 595 nm dichroic mirror split the fluorescence emission into two color channels. In the case of Alexa Fluor 488, a 525/50 nm emission filter was used to filter the green channel, and a 562/55 nm emission filter was used for Qdot 565. A 645/75 nm emission filter was used for Qdot 655. The detector focuses the signals from the two color channels on 50 µm core diameter fused silica optical fibers mounted on precision fiber couplers, connected to Single Photon Counting Modules (SPCMs, PerkinElmer Incorporated, Fremont, Calif.). The SPCMs incorporate an avalanche photodiode to provide high detection efficiency over a wide range of wavelengths. After transduction and amplification by the SPCMs, the signal may be autocorrelated using custom hardware and software (Correlator.com, Bridgewater, N.J.).

The fluidic channel and confocal microscope achieve a high signal to noise ratio as well as uniform excitation and rapid detection of all quantum dots and organic fluorophores in solution. The 500 nm square cross section of the channel provided both focal volume reduction and approximately uniform illumination across the channel width. The 210 zL focal volume was defined in two dimensions by the 500 nm width and depth of the channel, and the 830 nm length of the focal volume was a function of the 60X objective and 50 µm optical fibers used.

In one embodiment, an approximately uniform illumination profile may be achieved by underfilling the back aperture of the microscope objective to the extent that the focused laser spot is significantly larger than the 500 nm channel width. This produces a gaussian intensity profile across the channel width with a maximum intensity at the center of the channel and a reduction of illumination intensity of approximately 5% at the channel walls. This calculation was based on measurements of the 1/e value of the illumination profile. Because the entire channel width is illuminated, every quantum dot and organic fluorophore flowed through the focal volume. This increased detection efficiency when compared to other methods utilizing a focused laser spot smaller than the channel dimensions, or in free solution. In these cases, not every fluorescent molecule in solution is detected, and fluorophores that do enter the focal volume receive varying amounts of excitation depending on their interaction with the laser spot. Underfilling the objective also has a benefit of delivering as much laser power to the channel as possible while achieving the desired illumination profile.

Optical fibers may be used both as pinhole apertures and to couple the image of the channel to the avalanche photodiodes. The size of the optical fibers determines both the thickness of the focal plane and the length of the focal volume, and may have a significant impact on signal to noise ratio. 50 μm fibers may yield a higher signal to noise ratio than larger fibers, without undue signal rejection.

In a further example, before performing simultaneous multicolor detection, two single color quantum dot conjugates were detected both separately and together to verify the absence of spectral cross talk, defined as a false detection signal in one color channel caused by an actual detection event in the other. Qdot 565 Streptavidin Conjugates were detected in the green channel and Qdot 655 Streptavidin Conjugates were detected in the red channel. As each quantum dot conjugate passed through the focal volume, a burst of photons was emitted and detected. Photon bursts were analyzed using a peak-locating algorithm written in Matlab. This program searched for all peak maxima equal to or greater than a threshold value defined as three standard deviations above the mean background count rate, with a confidence limit of greater than 99%. The mean background was subtracted from bursts meeting this criterion. The width and height of each burst was measured and the bursts were integrated to determine the total number of photons collected.

Figure 3:
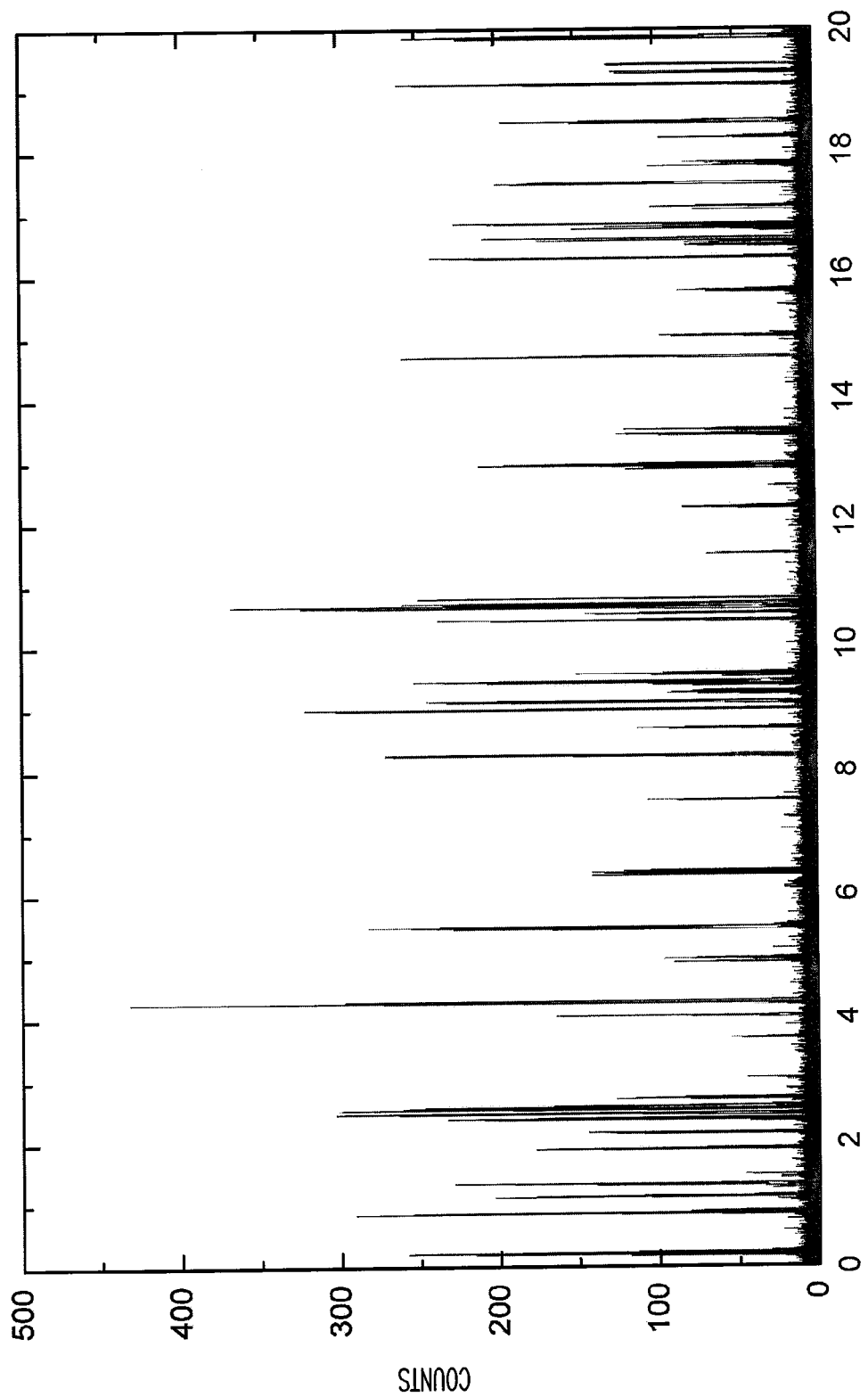
FIG. 3 illustrates bursts of green and red photons collected as two quantum dot conjugates passed through a detection volume according to an example embodiment.

In control experiments with conjugates of only one color, photon bursts attributed to quantum dots were detected in the expected channel, while the other channel exhibited nothing more than background noise (not shown). When the two quantum dot conjugates were mixed, bursts in both color channels were detected, as shown in FIG. 3. Detection events were visibly non-coincident, and PCH analysis was used to quantify the absence of spectral cross-talk. PCH analysis is a conceptually simple technique providing direct information about each detection event, coincident or otherwise, in both color channels. In the event of spectral cross-talk, detection of a quantum dot in one color channel would yield a simultaneous false positive signal in the other color channel. A histogram of the time shift between detection events in the two color channels would consequently display a sharp peak centered at zero. The time shift histogram (not shown), however, displayed a constant distribution of the time shift as a function of time indicates that the time shift between bursts detected in the two color channels was random.

Figure 4A:
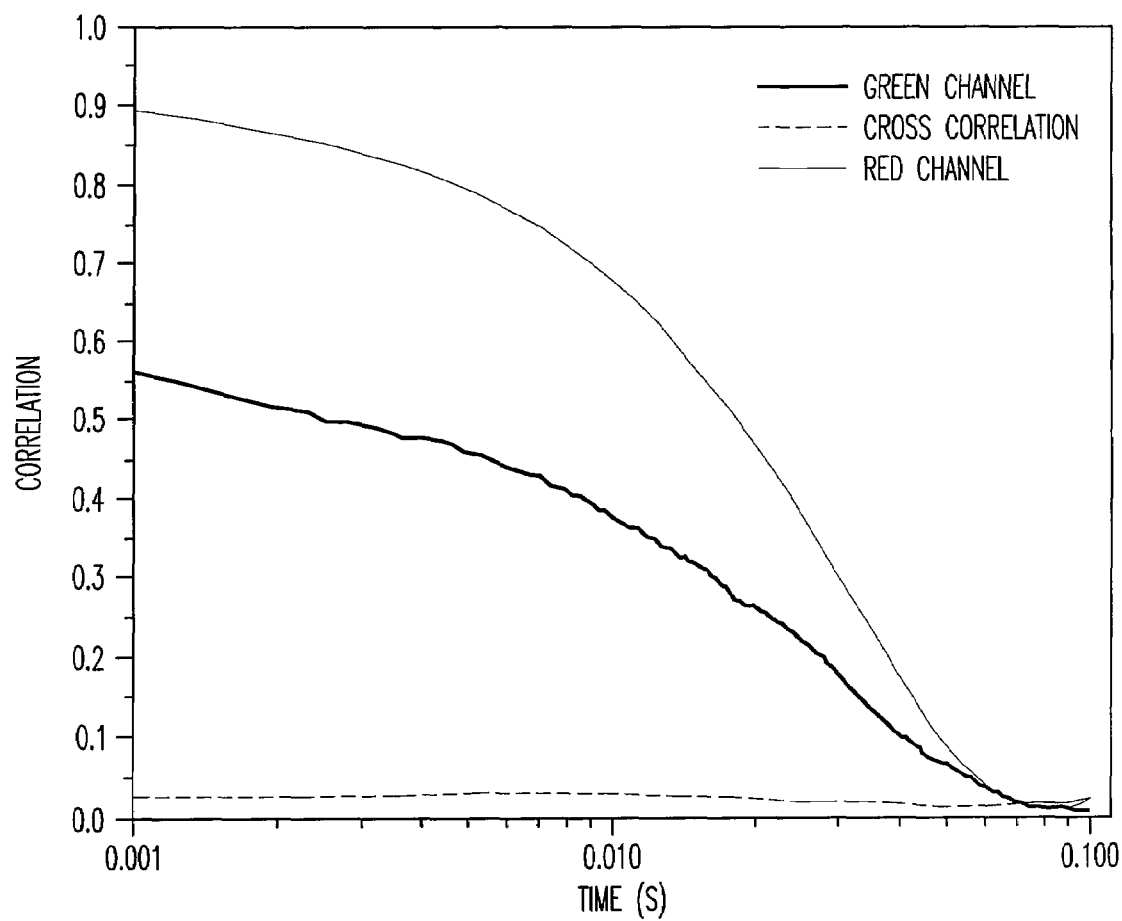
FIGS. 4A and 4B illustrate photon burst scans for Qdot 655 Streptavidin Conjugates bound to Alexa Fluor 488 according to an example embodiment.
Figure 4B:
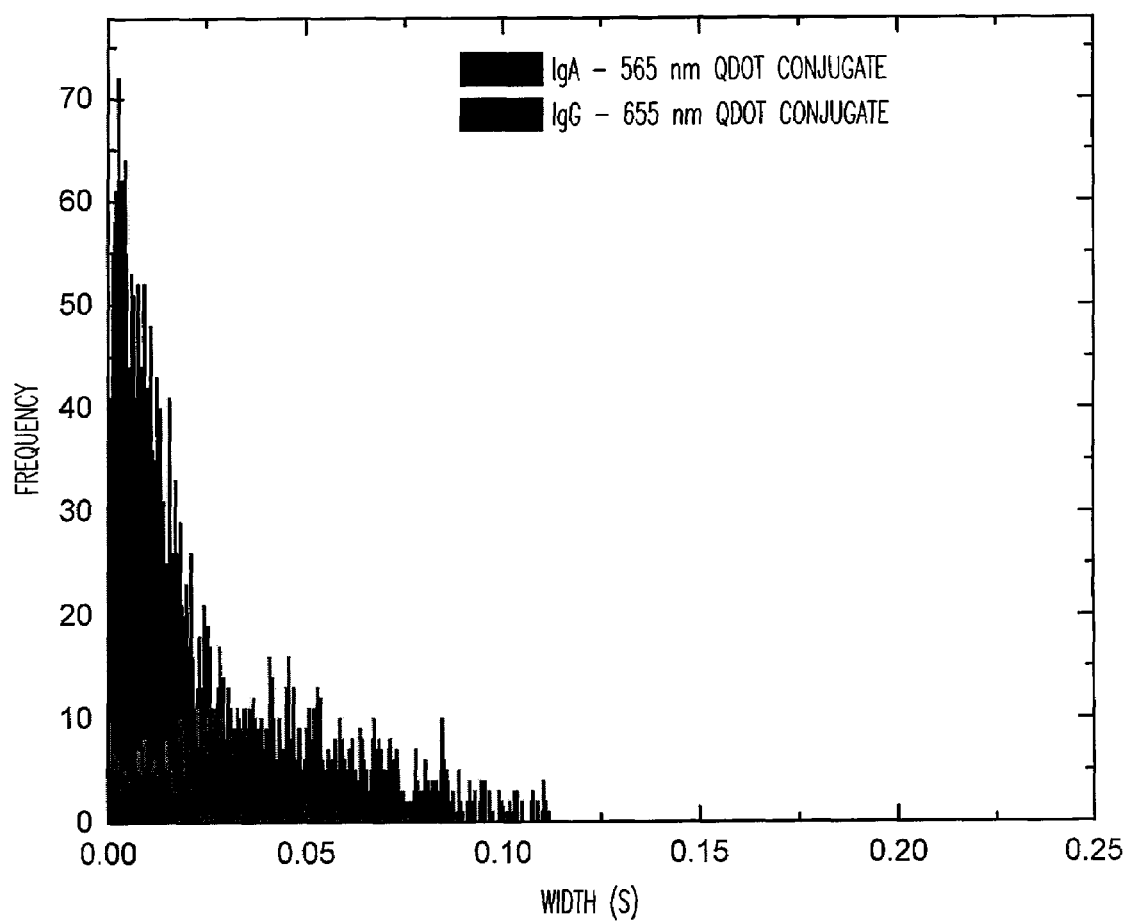
Figure 5:
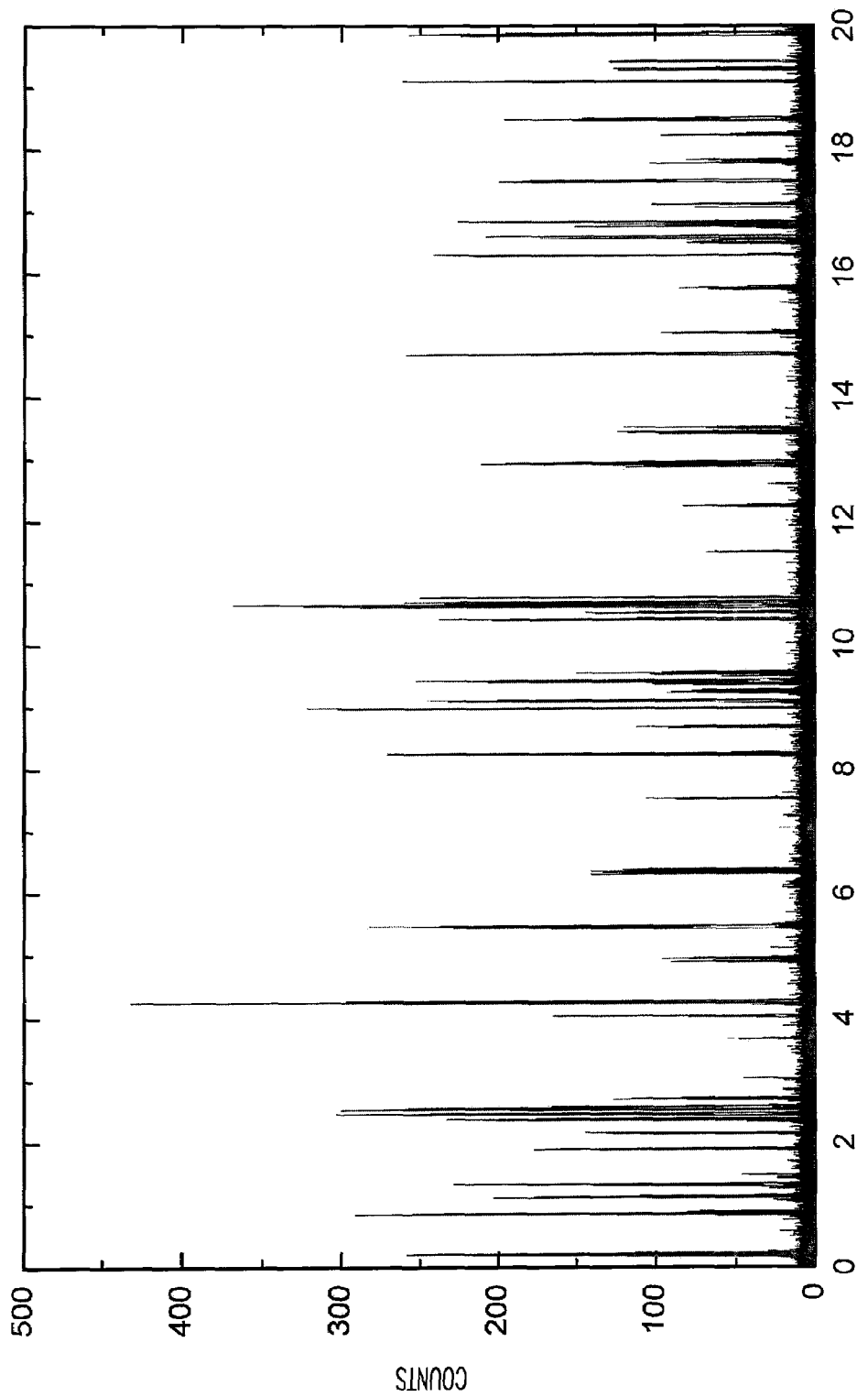
FIG. 5 is a time shift histogram for quantum dot and organic fluorophore detection events in two color channels according to an example embodiment.

After detection of single color quantum dot conjugates, quantum dots were conjugated with organic fluorophores, individually detected and analyzed. Fluorescence emission was collected simultaneously from Qdot 665 Streptavidin Conjugates and Alexa Fluor 488 molecules without significant signal rejection. Coincident detection between the two color channels was analyzed to determine the level of binding between Qdot 655 Streptavidin Conjugates and biotinylated DNA oligomers labeled with Alexa Fluor 488. Photon burst scans for the two color channels are shown in FIG. 4A, with a section expanded for clarity in FIG. 4B. In the expanded section, several coincident and non-coincident detection events are visible. A histogram of the time shift between detection events in the two color channels is shown in FIG. 5, with a peak centered at approximately zero, indicating coincident detection. This distribution was fit to a gaussian with a mean value of $-2.0 \cdot 10^{-5}$ s with a standard deviation of $1.6 \cdot 10^{-6}$ s. Detection events in the two color channels were considered to be coincident if the time shift between them was within three standard deviations of the mean. Non-coincident detection events from unbound quantum dots and organic fluorophores are reflected in the approximately uniform background to the sides of the peak. In this scan, 1,620±16 photon bursts were detected in the green channel and 2,093±21 photon bursts were detected in the red channel. 1,201±12 of these detection events were coincident, indicating that 74.1%±0.7% of the Alexa Fluor 488 labeled DNA oligomers were bound to 57.4%±0.6% of the Qdot 655 streptavidin conjugates.

In order to further characterize the degree of binding between the two species, the separate cases of coincident and non-coincident detection events in the two color channels were analyzed. To determine the number of quantum dots and organic fluorophores associated with each detected bound conjugate, the number of photons collected from coincident detection events was compared to the number of photons collected from non-coincident detection events. Because of the low concentration of the solution, non-coincident photon bursts in the two color channels were presumed with a high degree of confidence to be the result of single molecule detection. The number of photons emitted from the quantum dots and organic fluorophores was a function of the time spent crossing the focal volume, and so FCS was used to account for possible mobility differences.

In FCS, a fluctuating fluorescence intensity signal is autocorrelated to measure the temporal effects of changes in concentration, diffusion, flow and other time dependent photoprocesses. The normalized autocorrelation function for the fluorescence intensity is defined as:

$$G(\tau) = \langle \delta f(\tau) \cdot \delta f(t+\tau) \rangle / \langle f(\tau) \rangle^2 \tag{1}$$

In this equation, f(τ) is the fluorescence intensity as a function of time. In the case of a uniformly illuminated fluidic channel with electrokinetic drive, the autocorrelation function was approximated by a model accounting for triplet state population, one-dimensional diffusion and flow:

$$G(\tau) = 1/N \cdot (1 - F + F \cdot \exp(-\tau/T_b)) \cdot 1/(1+\tau/T_d)^{0.5} \cdot \exp(-\tau^2/(T_f^2(1+\tau/T_d))) \tag{2}$$

In this equation, N represents the number of molecules in the focal volume, F is the fraction of molecules in a triplet state, $T_b$ is the triplet state relaxation time, $T_d$ is the characteristic diffusion time and $T_f$ is the characteristic flow time. Autocorrelation curves were fit to this equation using the Levenberg-Marquardt method to extract parameter values. For the quantum dots, triplet state population was not found to be a relevant parameter when fitting the autocorrelation curves, as expected. Furthermore, because the full width at half maximum of the autocorrelation curves was on the order of 150 μs, autocorrelation data below 10 μs affected by fluorophore triplet state population was not fit to simplify determination of intercepts. $T_d$ and $T_f$ were allowed to float in all fitting routines. The time spent in the focal volume was within the error bars for free quantum dots and organic fluorophores, and bound conjugates. After mobility differences had been discounted, coincident bursts in the red detection channel were determined to have a mean value of 86 photons, whereas non-coincident red bursts had a mean value of 69 photons. Coincident bursts in the green detection channel had a mean value of 23 photons, while non-coincident bursts in the green channel had a mean value of 18 photons. This indicates that on average 1.25 quantum dots were detected bound to 1.28 organic fluorophores, giving a degree of binding of approximately one to one.

Figure 6:
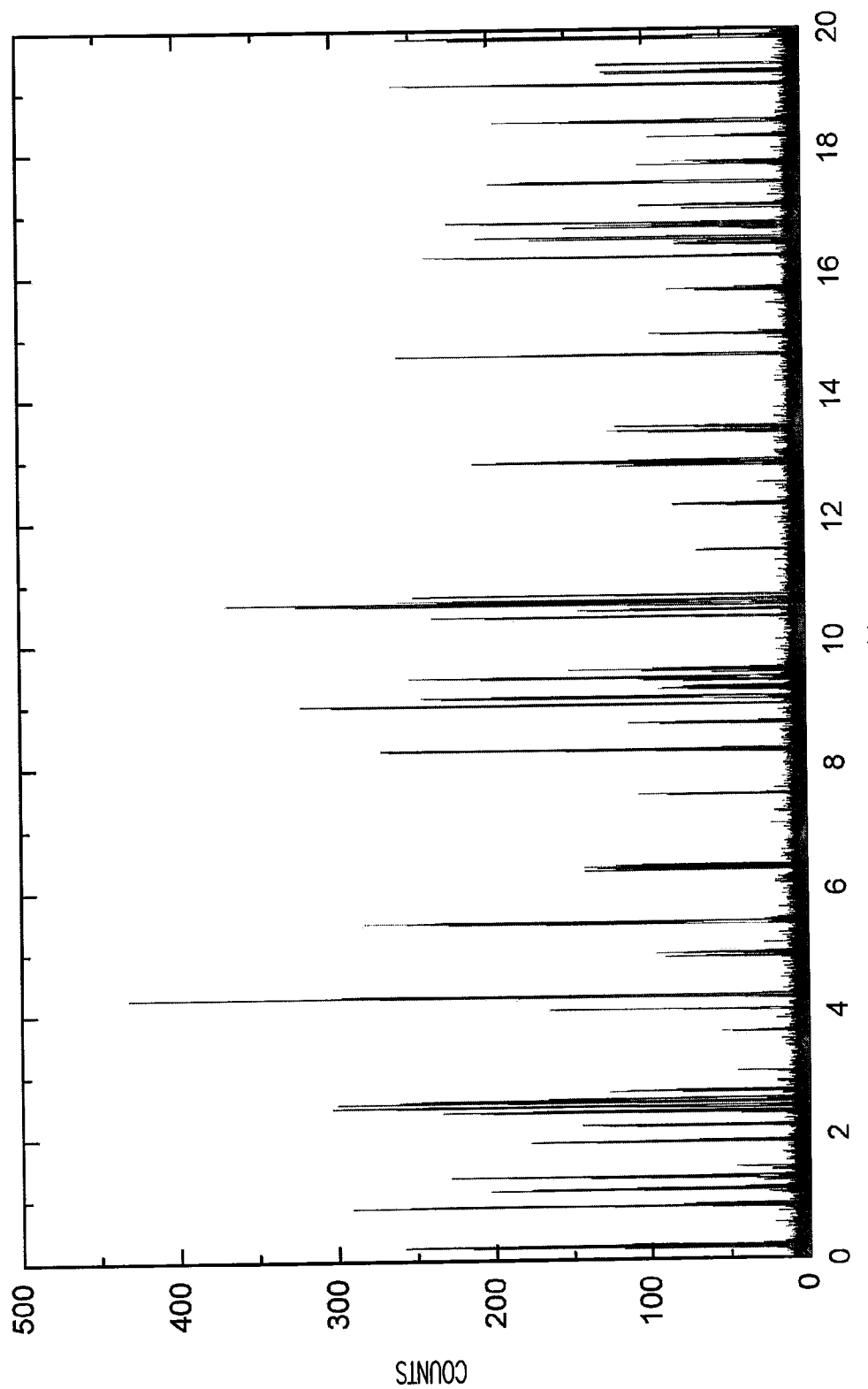
FIG. 6 illustrates burst area histograms for Qdot 655 Streptavidin Conjugates and Alexa Fluor 488 molecules according to an example embodiment.

The inherent brightness of the quantum dots was also evident in this example. Burst area histograms for Qdot 655 and Alexa Fluor 488 are shown together in FIG. 6. The average number of photons from Alexa Fluor 488 detection events was 21.7 photons with a standard deviation of 12.3 photons. The average value for Qdot 655 Streptavidin Conjugate detection events was 76.1 photons with a standard deviation of 71.2 photons.

Protein Example

In this assay, two proteins (IGG and IGA) were conjugated with quantum dot nanocrystals of different emission wavelengths. The two protein-quantum dot conjugates were subsequently mixed and driven electrokinetically through a nanofluidic channel. As the conjugates traversed the detection volume, a single light source excited both species, and the resulting fluorescent emission from the quantum dots was detected, amplified and analyzed. Spectral cross talk between the color channels was not observed.

Two species of quantum dots were used as labels for different protein molecules. The two protein-quantum dot conjugates were mixed and diluted to a concentration of several hundred pM to minimize the possibility of multiple analytes passing through the detection volume simultaneously. As the two conjugate species passed through the detection volume, they were excited with a single light source. Individual conjugates were easily detected, and cross correlation between the color channels was not observed.

Linking between quantum dots and proteins may be done in number of ways. In the case of streptavidin conjugates, the quantum dots may be covered with an unknown number of streptavidin linkers, each with multiple binding sites. This can result in multiple protein molecules attached to each quantum dot, which may compromise single molecule detection.

In one embodiment, the nanofluidic channels were fabricated using photolithographic processes in conjunction with a fusion bonding technique. This combination was chosen for its simplicity, high throughput and low cost. Design and layout of the devices was done with L-Edit v10.0 (Tanner Research Incorporated, Pasadena, Calif.), and exported using a GDSII format for photomask patterning. A chromium mask was subsequently exposed using a Mann/GCA PG3600 pattern generator. After exposure, the mask was developed in Shipley Microposit for 1 minute, chromium etched for 2 minutes, and bathed in Shipley 1165 for 30 minutes to remove residual photoresist.

In order to increase photoresist adhesion, the substrate wafers were treated in an HMDS vapor prime oven (Yield Engineering Systems Incorporated, San Jose, Calif.) prior to spin deposition of photoresist. A thin film of Shipley 955i photoresist was spun onto the substrate wafer at 3,000 RPM for 30 seconds and immediately pre-baked on a hot plate at 90° C. for one minute. The channels were then exposed using a GCA Autostep 200 optical stepper. Before development in Shipley Microposit developer, a 115° C. post-exposure bake for one minute ensured good resolution. A $CF_4$ reactive ion etch was performed using the photoresist as an etch mask. The etch depth of the devices varied from 450 to 550 nm. Etching to a depth smaller than the channel width resulted in some degree of automatic filtration to prevent clogs, often an issue in nanofluidic devices.

After the channel etching was complete, a thick layer of Shipley 1827 photoresist was spun on to the substrate wafer to protect device features during powder blasting. Inlet and outlet holes were blasted through the substrate using an alumina powder blaster. After the inlet and outlet holes were excised, the substrate wafer was sonicated in acetone and isoproponal for 10 minutes and blown dry with $N_2$.

In order to prepare the substrate and cover wafer surfaces for bonding, a multistage RCA clean was performed. The first stage of the RCA clean was a base bath, consisting of a standard ratio of 5 parts water, 1 part ammonium hydroxide, and 1 part hydrogen peroxide heated to 75° C. The base bath removed metals and other inorganic contamination from the wafer surfaces, and was followed by a cascading de-ionized water rinse. The next stage of the RCA clean was an acid bath, consisting of 5 parts water, 1 part hydrogen chloride, and 1 part hydrogen peroxide heated to 75° C. This removed organic contamination from the wafer surfaces, and was followed by a cascading de-ionized water rinse. The third step of the RCA clean was a second base bath and water rinse. In addition to removing any further contamination, this final chemical process left the wafer surfaces terminated in hydroxyl groups, which greatly aided the bonding process. The base and acid baths lasted for 10 minutes each, and the wafers were rinsed until the resistance of the water bath reached at least 15 MΩ. The wafers were placed in a spin-dryer for a final water rinse and dry.

After the wafers were cleaned and dried, they were placed on top of each other, in physical contact. Slight mechanical pressure was applied to the center of the wafer stack, resulting in a radial bond wave propagating out from the center of the wafers. After the initial van der Waals bond had been formed, the wafers were annealed at 1100° C. for 16 hours. Care was taken to load and unload the wafers slowly to minimize the effects of thermal stress, and to ramp the temperatures up from and back down to the standby loading temperatures slowly. The array of nanofluidic channels is very similar to that shown at 200 in FIG. 2A.

Nanoport fluidic connectors (Upchurch Scientific, Oak Harbor, Wash.) were attached to the wafers on top of the inlet reservoir, and polyethylene reservoirs were attached to the waste outlet of the devices.

Commercially available protein-quantum dot conjugates were purchased (Quantum Dot Corporation, Hayward, Calif.). IGG labeled with Qdot 565 via secondary antibody conjugates was used in the green detection channel while Qdot 655 conjugated with IGA was used in the red detection channel.

An inverted confocal microscope setup was used for this single molecule study as illustrated in FIG. 2A. The entire setup was mounted on a floating optical table (TMC, Peabody, Mass.) to isolate the microscope, laser and optical equipment from vibrations. An Olympus IX-71 inverted microscope (Olympus America, Melville, N.Y.) with an integrated Prior Pro-Scan stage (Prior Scientific Incorporated, Rockland, Mass.) formed the core of the experimental setup. An Argon-Krypton mixed gas tunable laser (Melles Griot Laser Group, Carlsbad, Calif.) was selected for its wide range of operating wavelengths. Between the laser aperture and microscope, a number of optical elements were used to guide and tune the laser beam. Unless otherwise specified, all optics and optomechanics were furnished by Newport Corporation, Irvine, Calif.

The optical components included a neutral density filter set (Thorlabs Incorporated, Newton, N.J.) to attenuate laser power when desired, mirrors situated in kinetic mounts to precisely steer the laser beam, and irises for beam alignment. For single molecule detection in a nanofluidic channel, the back aperture of the objective was underfilled in order to deliver maximum laser power along with an approximately uniform laser profile across the channel. A schematic of the nanofluidic channel and detection volume as defined by the focused laser is also represented in FIG. 2B. The focused laser spot was determined to have a 1/e size of 1.4 μm, from bulk diffusion measurements (not shown) of dUTP labeled with Alexa Fluor 488 (Molecular Probes Incorporated, Eugene, Oreg.).

Upon entering the microscope, the laser beam encountered the first set of filters. A 497 nm dichroic mirror reflected the 465 nm laser light towards the sample, where an Olympus UPlanAPO 60X coverslip-corrected water immersion objective was used both to focus the laser beam on the nanofluidic channels for excitation and to collect emitted fluorescence from the conjugates. Light collected with the objective was directed back through the dichroic mirror to a 520 nm long pass barrier filter. The emission signal was then directed to a second set of filters. A 595 nm dichroic mirror split the emission into two color channels, red and green, with 645/75 nm and 562/55 nm barrier filters cleaning up the two channels, respectively. After passing through the last filters, the two color channels were focused on 200 μm core diameter fused silica optical fibers, mounted on precision fiber couplers (Thorlabs). The fibers were then connected to Single Photon Counting Modules (SPCMs, PerkinElmer Incorporated, Fremont, Calif.). The SPCMs incorporate a silicon avalanche photodiode to provide high detection efficiency over a wide range of wavelengths. After transduction and amplification by the SPCMs, the signal was autocorrelated using custom hardware and software (Correlator.com, Bridgewater, N.J.).

In order to fill and drive the devices, a combination of hydrostatic pressure and electrokinetic flow was used. Precision regulators (Omega Engineering Incorporated, Stamford, Conn.) were used to control the pressure delivered from a tank of compressed nitrogen (Airgas Incorporated, Radnor, Pa.). Unless otherwise specified, all fluidic connectors were purchased from Upchurch Scientific, Oak Harbor, Wash. Pressure was applied to custom in-line reservoirs to rapidly fill the channels via the nanoport connections. Once the nanofluidic channels were filled, both the inlet and outlet reservoirs with filled with solution, and gold electrodes were placed in contact with the solution to enable electrokinetic drive of the solution.

Figure 7:
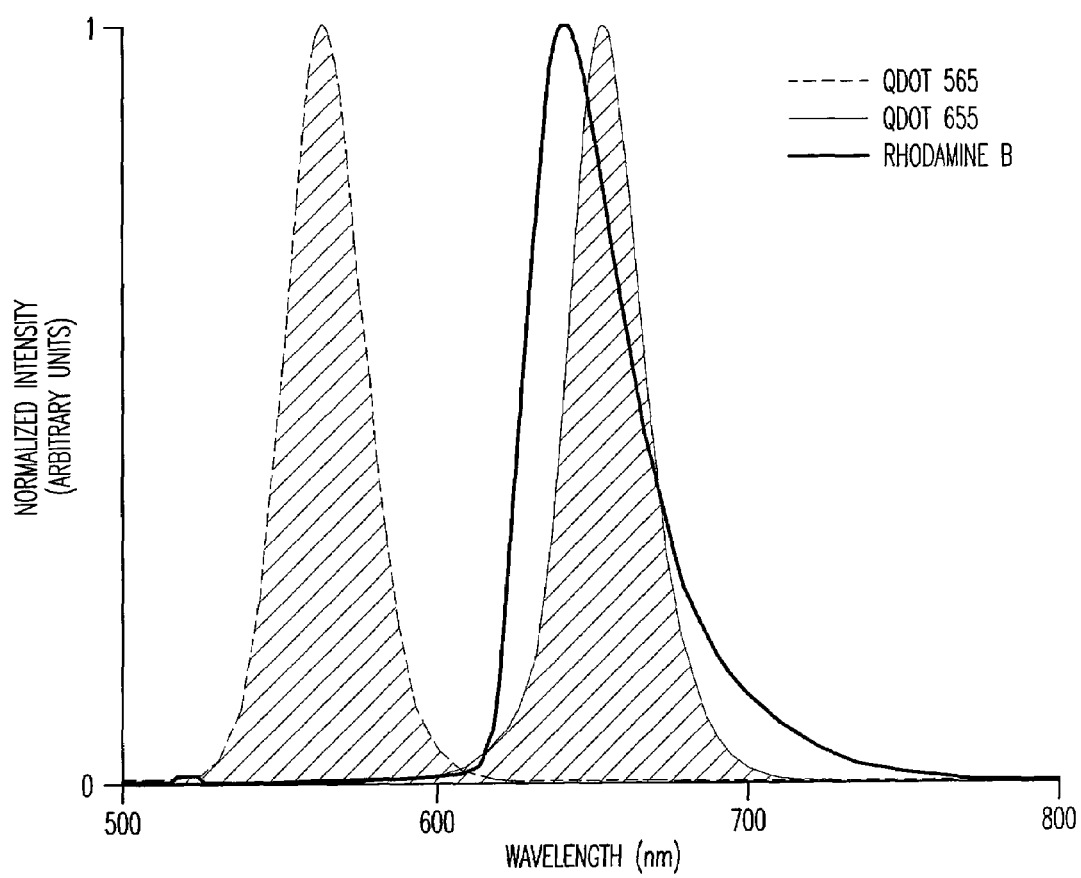
FIG. 7 illustrates emission spectra of Qdot 565, Qdot 655 and Rhodamine B according to an example embodiment.

Dye selection plays an important role in single molecule studies. Ionic dyes, the standard choice in fluorescence microscopy assays, have several advantageous properties that make them well suited to single molecule studies. These include fluorescence quantum efficiencies approaching unity and fluorescence lifetimes below 10 ns. Accordingly, xanthene dyes such as Rhodamine 6G and tetremethylrhodamine isothyiocyanate are commonly used in single molecule studies. It is also becoming increasingly popular to use naturally occurring fluorescent proteins in single molecule studies. For example, Green Fluorescent Protein is resistant to photobleaching because its chromophore is located within the interior of its "β-can" structure and is thus protected from molecular oxygen. Unfortunately, despite their many advantages, almost all of these organic dyes exhibit broad emission spectra. FIG. 7 shows an example of such a spectrum for Rhodamine B. These broad emission spectra make multifluorophore single molecule studies virtually impossible. An excellent alternative to organic dyes, and the subject of this paper, is semiconductor nanoparticles or quantum dots.

Quantum dots tend to be highly photostable, with fluorescence decay lifetimes ranging from nanoseconds to microseconds. Hence, these particles are ideal for single molecule spectroscopy due to their improved spectral properties when compared to typical organic dyes. Quantum dots such as CdSe also tend to have a much narrower full width at half maximum and much more symmetrical emission spectra when compared to their organic counterparts. The benefits can be clearly seen in FIG. 7 in which the emission spectra of Qdot 565 and Qdot 655 are plotted. There is no overlap between both spectra, making a two color single molecule study error free in the sense that there is no cross talk between the red and green channels. If standard organic fluorophores were used, this would not be possible, as overlap in emission spectra would directly result in a false positive signal in a given detection channel. When organic fluorophores are used in a multicolor experiment the collected photons are typically restricted to a specific region of the emission spectra in order to ensure no cross talk between channels. This results in lower overall signal intensities and detection efficiency. On the other hand, the entire emission spectrum of quantum dots is utilized as the spectral full width at half maximum can be as low as 40 nm.

In addition to detecting the entire emission spectrum of each protein-quantum dot conjugate, care was taken to illuminate the entire nanofluidic channel in an approximately uniform manner, enabling the maximum emission of photons from and complete detection of all protein-quantum dot conjugates in solution. This greatly increases detection efficiency when compared to other methods utilizing a focused laser spot smaller than the channel dimensions.

Figure 8:
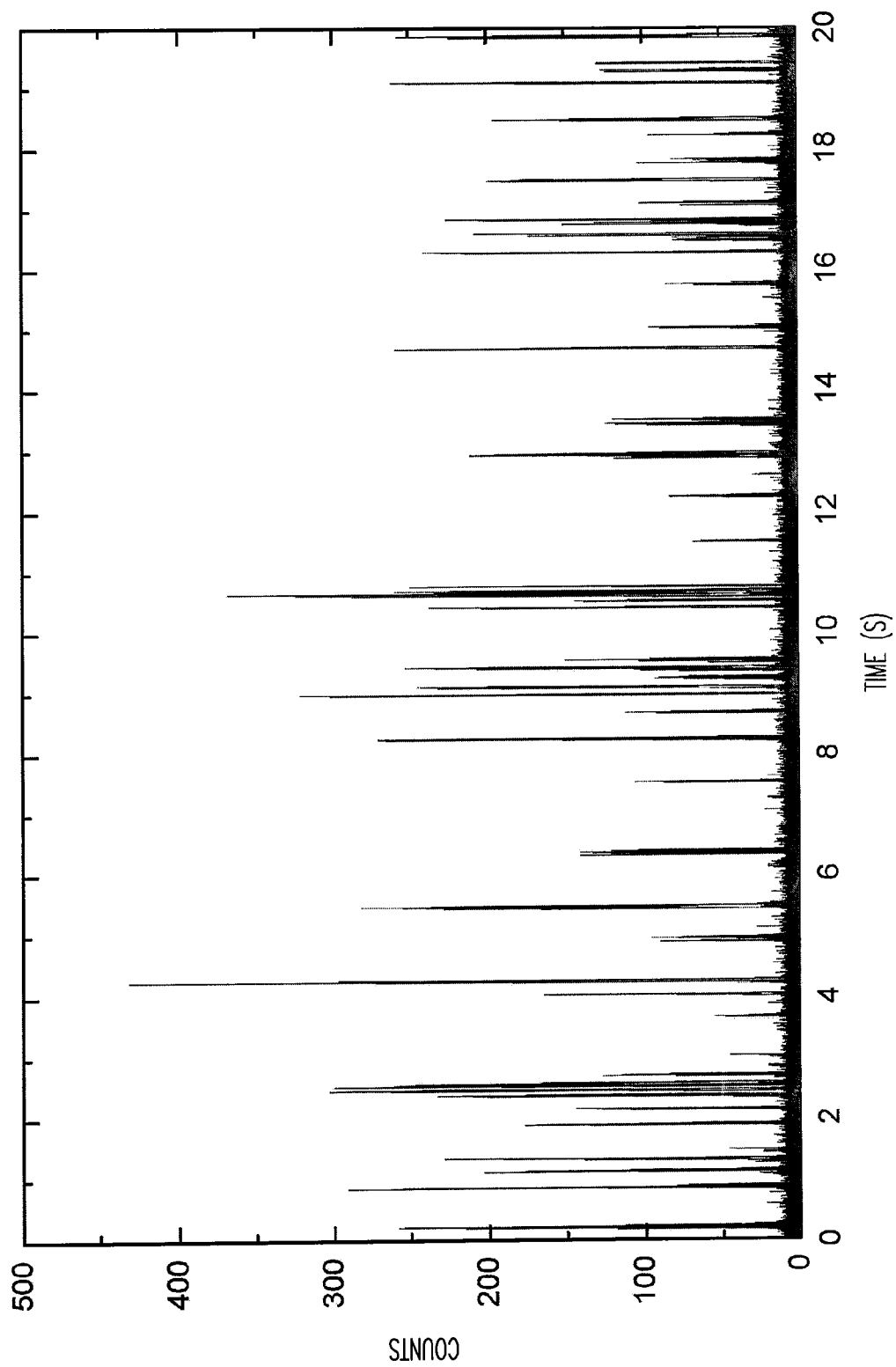
FIG. 8 illustrates burst acquisitions as red and green quantum dot conjugates pass through the observation volume and are excited and emit fluorescence according to an example embodiment.

Single particle photon burst scans for a 50/50 mixture of IgA conjugated with Qdot 565 and IgG conjugated with Qdot 665 is shown in FIG. 8. The 607-682 nm channel is plotted in red and the 534-589 nm channel is plotted in green. Qualitatively there appears to be negligible cross-talk between the red and green channels, resulting in a low error rate when distinguishing between IgA and IgG at the single molecule level. The overall difference in signal intensities is attributed to several factors. The primary reason is that the absorption cross sections of the red protein-quantum dot conjugates is higher than the green protein-quantum conjugates at the excitation wavelength of 465 nm. With this in mind, the burst heights are expected to have an inherent difference in width and area. A secondary effect on the burst height originates from varying fluorescence quantum yields. For the acquisitions shown in FIG. 8, the average burst height for the red conjugate was 227 counts with a relative standard deviation (RSD) of 61%. The bin time in all plots was 400 μs when the particles were driven electrokinetically at 200 V. For the green conjugates under identical conditions, an average burst contained 46 counts and the RSD was 75%. In both cases these values were calculated from a minimum of 1000 bursts over a 65 s period.

Burst widths for the red and green channels were calculated using a peak-locating algorithm written in Matlab. The program searched for all peak maxima above a specific threshold value which was defined as three standard deviations from the mean background count rate. The peaks were then integrated to determine the total number of counts. The widths were determined by calculating the total number of bins used for a single particle burst.

Figure 9:
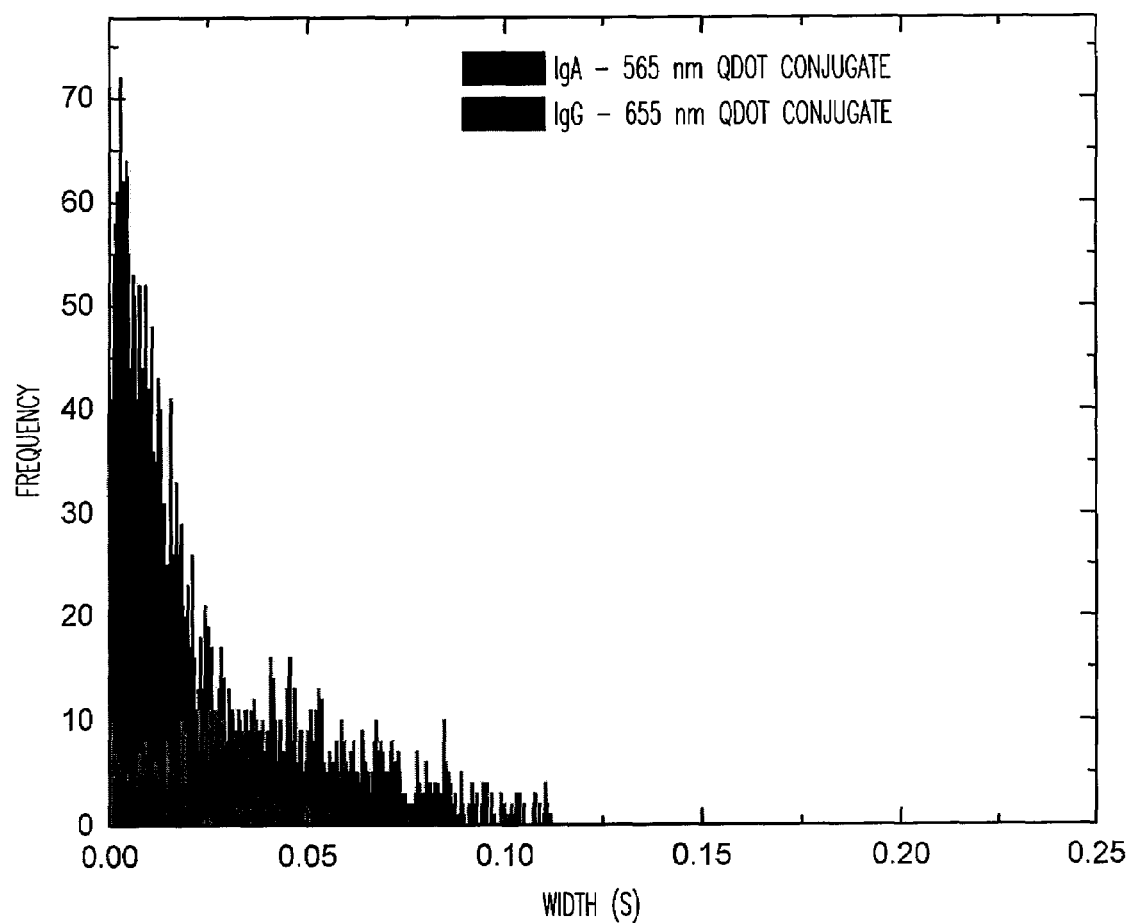
FIG. 9 illustrates burst width histogram for green and red quantum dots according to an example embodiment.

Burst width histograms for both the red and green channels are shown in FIG. 9. In all cases a minimum of 1000 particle bursts were used in the calculation of the distributions. Clear statistical differences are observed between the red and green channels. For example, the red conjugates had mean burst widths of 57 ms, while the mean burst width for the green channel was 17 ms. This decrease in residence time is related to the different transit times of the two conjugate species. In both cases the RSD was well below 70%. The clear difference in burst width values implies that the emission spectra of the red and green quantum dots have sufficiently narrow full width at half maximum resulting in virtually no cross talk between the two detection channels.

Figure 10:
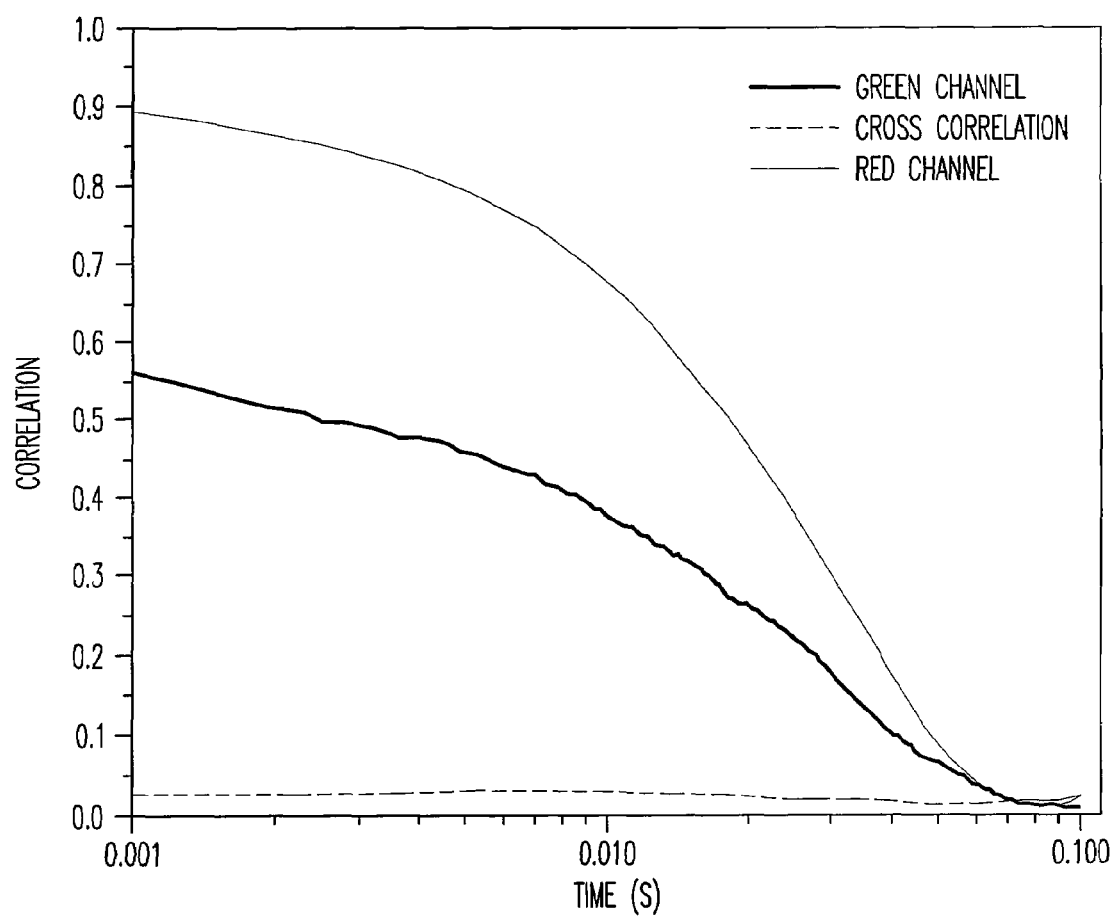
FIG. 10 illustrates auto- and cross-correlation curves for two quantum dot conjugates according to an example embodiment.

Confirmation that there is negligible cross talk between the red and green detection channels can be demonstrated by performing a cross-correlation analysis. Cross-correlation is an extremely sensitive method for detecting the presence of fluorescence bursts in single molecule experiments. This analysis method cross-correlates the average of a fluctuating signal as opposed to the mean spectral intensity. The concept relies on analysis of local concentration fluctuations in a small volume, and is a measure of the temporal fluorescence intensity fluctuations of a dilute system. FIG. 10 shows the cross-correlation curve between the red and green channels as well as the autocorrelation of the individual green and red channels respectively. The cross-correlation intensity is continuously less than 0.1 with no apparent trend. This emphasizes the fact that both conjugates were distinguishable without sacrificing photon collection efficiency, as the entire emissive range is used in the photon traces for the red and green detection channels. As a control, rather than using a mixture of the different protein-quantum dot conjugates, experiments were performed with solutions containing only one type of conjugate. This confirmed that there was indeed no cross talk between the red and green channels as the channel of interest would contain single particle bursts while the other channel would strictly have photon counts associated with the shot noise of the system.

CONCLUSION

A fluidic channel fabricated in fused silica with an approximately 500 nm square cross section was used to isolate, detect and identify individual quantum dot conjugates. The channel enabled the rapid detection of every fluorescent entity in solution. A laser of selected wavelength was used to excite multiple species of quantum dots and organic molecules, and the emission spectra were resolved without significant signal rejection. Individual quantum dots were detected separately as a control and together to verify the absence of spectral cross talk. Quantum dots were then conjugated with organic molecules and detected to demonstrate efficient multicolor detection. PCH was used to analyze coincident detection and to characterize the degree of binding. The use of a small fluidic channel to detect quantum dots as fluorescent labels was shown to be an efficient technique for multiplexed single molecule studies. While the small fluidic channel was described as approximately 500 nm square cross section, other sizes, such as smaller square cross sections that limit the number of molecules flowing through it at any one time, may also be used. Detection of single molecules allows use of even smaller sample sizes, helping to conserve small samples. Detection of single molecule binding events has a variety of applications including high throughput immunoassays.

By demonstrating the detection of two species of protein molecules conjugated with quantum dot nanocrystals of different emission wavelengths, this assay has added to the toolbox of techniques available for single molecule studies. The combination of quantum dots as bio-labels and nanofluidic channels as a means to increase SNR, acquisition rates and statistical accuracy shows great promise in future multicolor single molecule studies.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The invention claimed is:

1. A method comprising:
conjugating molecules with a plurality of different types of quantum dots having different emission spectra to form conjugates;
driving the conjugates through a sub-micrometer channel detection volume;
exciting the conjugates in the sub-micrometer channel; and
detecting emission from multiple regions of the spectrum.

2. The method of claim 1 wherein the conjugates are excited by illumination with a single light source.

3. The method of claim 2 wherein the light source comprises a laser that provides substantially uniform light across an entire width of the sub-micrometer channel.

4. The method of claim 1 wherein the quantum dots comprise CdSe.

5. The method of claim 1 wherein the types of quantum dots comprise green light and red light emitting quantum dots.

6. The method of claim 1 wherein there is substantially no emission spectral overlap between the different types of quantum dots.

7. The method of claim 1 wherein the sub-micrometer channel has a width of approximately 500 nm.

8. The method of claim 7 wherein the sub-micrometer channel has a depth of approximately 500 nm.

9. The method of claim 1 wherein the conjugates are driven through the sub-micrometer channel electrokinetically or hydrostatically, or a combination of both.

10. The method of claim 1 wherein the quantum dots comprise Qdot 565 and Qdot 655.

11. The method of claim 10 wherein the molecules comprise IGG and IGA.

12. The method of claim 1 wherein the detected emission is amplified.

13. The method of claim 1 wherein the emission is fluorescent.

14. The method of claim 1 wherein the different types of quantum dots display a large Stokes shift.

15. The method of claim 1 wherein the channel detection volume is sized to flow single molecules.

16. The method of claim 1 wherein the channel is formed of mirror-polished fused silica.

17. The method of claim 1 wherein emission are detected with use of an inverted confocal microscope.

18. A method comprising:
driving molecules, conjugated with one or more quantum dots with known emission spectra to form conjugates, through a channel sized to promote single molecule flow;
exciting the conjugates in the channel; and
detecting emissions from excited conjugates to identify the molecules.

19. The method of claim 18 wherein detection is performed with use of an inverted confocal microscope.

20. A method comprising:
- confining molecules, conjugated with one or more quantum dots having known emission spectra to form conjugates, within a detection volume;
- exciting the conjugates in the detection volume; and
- detecting emissions from individual excited conjugates in the detection volume to identify the molecules.

21. The method of claim 20 wherein the detection volume comprises a sub-micron channel sized to promote single molecule flow.

22. The method of claim 20 wherein detecting emissions from individual excited conjugates comprises using a confocal microscope with high numerical aperture optics to confine collection of fluorescence to a desired depth of focus.

23. The method of claim 22 wherein the detection volume comprises a sub-micron channel sized to promote single molecule flow and the desired depth of focus is within the channel.

* * * * *